(12) United States Patent
Zalevsky et al.

(10) Patent No.: US 11,800,979 B2
(45) Date of Patent: Oct. 31, 2023

(54) SYSTEM AND METHOD FOR CALCULATING A CHARACTERISTIC OF A REGION OF INTEREST OF AN INDIVIDUAL

(71) Applicant: BAR ILAN UNIVERSITY, Ramat Gan (IL)

(72) Inventors: Zeev Zalevsky, Rosh HaAyin (IL); Aviya Bennett, Netanya (IL); Yevgeny Beiderman, Tel Aviv (IL); Sergey Agdarov, Rishon le-Tsiyon (IL); Yafim Beiderman, Tel Aviv (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 546 days.

(21) Appl. No.: 16/769,054

(22) PCT Filed: Dec. 2, 2018

(86) PCT No.: PCT/IL2018/051319
§ 371 (c)(1),
(2) Date: Jun. 2, 2020

(87) PCT Pub. No.: WO2019/111246
PCT Pub. Date: Jun. 13, 2019

(65) Prior Publication Data
US 2021/0169333 A1    Jun. 10, 2021

Related U.S. Application Data

(60) Provisional application No. 62/594,039, filed on Dec. 4, 2017.

(51) Int. Cl.
*A61B 5/00*    (2006.01)
*A61B 3/16*    (2006.01)
*A61B 5/11*    (2006.01)

(52) U.S. Cl.
CPC .............. *A61B 5/0051* (2013.01); *A61B 3/16* (2013.01); *A61B 5/004* (2013.01); *A61B 5/0091* (2013.01);
(Continued)

(58) Field of Classification Search
CPC ......... A61B 3/16; A61B 5/004; A61B 5/0051; A61B 5/0059; A61B 5/0091; A61B 5/1128; A61B 5/7246; A61B 5/7257
See application file for complete search history.

(56) References Cited

U.S. PATENT DOCUMENTS 8,638,991 B2   1/2014  Zalevsky et al.
9,244,041 B2   1/2016  Gallippi et al.
(Continued)

OTHER PUBLICATIONS

Bennett, et al. "Approach to breast cancer early detection via tracking of secondary speckle patterns reflected from the skin with artificial intradermal impurity" Dec. 1, 2017, Biomedical Optics Express, 5359-5367 (Year: 2017).*
(Continued)

*Primary Examiner* — Patrick Fernandes
*Assistant Examiner* — Anna Roberts
(74) *Attorney, Agent, or Firm* — BROWDY AND NEIMARK, P.L.L.C.

(57) ABSTRACT

An aspect of some embodiments of the present invention relates to a method for determining one or more characteristics of a region of interest. The method includes providing stimulation for exciting the region of interest for a first selected time period; monitoring mechanical response of the region of interest for at least a second time period after said first time period; processing data indicative of said mechanical response, and determining data on one or more measures of motion of the region of interest; utilizing data on one or more measures of motion for yielding at least one damping parameter indicative of damping of the mechanical response
(Continued)

of the region of interest, and determining at least one characteristic of the region of interest in accordance with at least one damping parameter.

21 Claims, 13 Drawing Sheets

(52) U.S. Cl.
CPC .......... *A61B 5/1128* (2013.01); *A61B 5/7246* (2013.01); *A61B 5/7257* (2013.01)

(56) References Cited

U.S. PATENT DOCUMENTS

| | | | |
|---|---|---|---|
| 9,636,041 B2 | 5/2017 | Zalevsky et al. | |
| 9,726,647 B2* | 8/2017 | Walker | G01N 29/4436 |
| 2009/0216131 A1* | 8/2009 | Chase | A61B 5/0051 |
| | | | 600/476 |
| 2013/0024136 A1* | 1/2013 | Gallippi | G01N 29/343 |
| | | | 702/41 |
| 2013/0197401 A1* | 8/2013 | Sato | A61N 7/00 |
| | | | 601/2 |
| 2014/0148658 A1* | 5/2014 | Zalevsky | A61B 3/102 |
| | | | 600/301 |
| 2016/0135788 A1 | 5/2016 | Greenleaf et al. | |

OTHER PUBLICATIONS

Moon, Woo Kyung, et al. "Computer-Aided Diagnosis Based on Speckle Patterns in Ultrasound Images" 2012, Ultrasound in Med. & Bio., vol. 38, No. 7, pp. 1251-1261 (Year: 2012).*

Margalit, et al., New method for remote and repeatable monitoring of intraocular pressure variations, Journal of Biomedical Optics, Feb. 2014, pp. 027002-1-027002-8, vol. 19(2).

* cited by examiner

SYSTEM AND METHOD FOR CALCULATING A CHARACTERISTIC OF A REGION OF INTEREST OF AN INDIVIDUAL

TECHNOLOGICAL FIELD

The invention relates to the field of medical devices and provides a system and method for determining biomechanical characteristics of tissue. The technique may be relevant for determining an amount of intro-ocular pressure, and monitoring of a breast cancer condition.

BACKGROUND ART

References considered to be relevant as background to the presently disclosed subject matter are listed below:
 [1] I. Margalit, Y. Beiderman, A. Skaat, E. Rosenfeld, M. Belkin, R. P. Tornow, V. Mico, J. Garcia and Z. Zalevsky, "A new method for remote continuous monitoring of intraocular pressure variations," J. of Biomedical Optics 19 (2), 027002 (Feb. 6, 2014).

Acknowledgement of the above references herein is not to be inferred as meaning that these are in any way relevant to the patentability of the presently disclosed subject matter.

BACKGROUND

Glaucoma is the second leading cause of blindness worldwide, disproportionately affecting women and Asians. It is caused by increased Intra-Ocular Pressure (IOP) and might result in damage to the eye's optic nerve, vision loss and eventually irreversible blindness if left undiagnosed and untreated. The general cause of glaucoma is a failure of the eye to maintain a proper balance between the amount of intra-ocular fluid formed, and the amount which drains out.

The IOP is a dynamic physiological variable with regular circadian modification and random variation over short and long periods, as muscle tone and the physiological condition of the subject alternate. Therefore, accurate monitoring of IOP is a fundamental clinical aspect in glaucoma care. Although many clinical decisions are based on IOP, current handling of glaucoma only contains periodic measurements of IOP during specific hours of the day. This is a suboptimal resolution, which presents an incomplete characterization of the variable nature of IOP.

Goldmann applanation tonometry (GAT) is the most commonly used ophthalmic instrument for IOP examination. Although GAT is very accurate, it is affected by inner-individual variations due to diversity in corneal thickness and rigidity, while being an invasive procedure, which forces the use of anesthetic eye drops, with limitations for monitoring the IOP over time. An alternative way of measuring IOP is by an air puff or a noncontact tonometer. Such a tonometer measures the IOP on the basis of the eye's resistance to the blow. By using this technique, an invasive procedure is avoided, but it is still unable to monitor the IOP over long periods of time, for obtaining more complete IOP profiles.

This limitation has encouraged researchers to develop new methods for IOP continuous monitoring. Several examples are of implants with telemetric pressure transducers, sensing contact lenses, implantable micro-fluidic devices, ocular telemetry sensors, and optical based principles devices.

Breast cancer is one of the major causes of death among women. The lifetime risk of a woman developing this disease has been established as one in eight. The most effective way to reduce breast cancer death is to treat the disease as early as possible. Most primary breast cancers are detected by the patients themselves when the tumor/lump reaches average size of about 2.5 cm, which leads to a survival rate of about 75%. However, early detection, e.g. when the tumor/lump is about 0.5 cm in size, together with suitable treatment, may increase the survival rate to about 95%. Hence, finding an accurate, simple and effective diagnostic method is extremely relevant. Breast palpation has found to be a simple and brief clinical screening test for breast cancer. In addition, there is general agreement that screening mammography reduces the rate of death from breast cancer among women. However, studies show that screening can be over-diagnosed, causing women to undergo surgery, radiation therapy, hormonal therapy, chemotherapy, or usually a combination of these treatments. Moreover, the sensitivity of mammography ranges from approximately 70% to 90% and has a high false diagnosis ratio for cancer. Therefore, further improvement in mammographic sensitivity is needed. Another tool for breast cancer diagnosis is MRI, which provides high soft tissue contrast, but this tool has to be made more practical for application in breast imaging.

Another optical tool is diaphanoscopic which is based on the difference in absorption coefficients of various tissues. It enables the detection of non-homogeneities in the breast. The areas of dense tumor look darker, while the pockets of cyst look clearer as compared to the surrounding tissues. However, breast cancer detection rate using this method is about 30%. Ultrasound Tagging of Light (UTL) has proved to be useful in the detection of breast cancer. Photon localization in turbid tissue is achieved by cross-modulating a laser beam with focused, pulsed ultrasound. Light which passes through the ultrasound focal spot is 'tagged' with the frequency of the ultrasound pulse. However, much work remains to be done to prove the feasibility of the UTL technique as a breast cancer imaging system.

Near-infrared spectroscopy has gained importance for non-invasive or minimally invasive cancer diagnostic applications in cancer. It is based on differences of endogenous chromophores between cancer and normal tissues. The method provides diagnosis and therapy monitoring of several cancers. Optical coherence elastography was also examined with a view to diagnose breast cancer. Tumors were identified by obtaining higher Young's modulus.

Generation of speckle patterns is a common phenomenon in coherent imaging systems and is an artifact degrading target visibility. It is specifically apparent when a coherent source and a detector are used to interrogate a medium, which is rough on the scale of the wavelength. Previous research has used monitoring of secondary speckle patterns in order to determine tissue characteristics. Such techniques utilize measurements of variation in speckle contrast with the location of ultrasonic column enabling detection of optical inhomogeneities inside the tissue.

U.S. Pat. No. 8,638,991 presents a method for imaging an object. The method comprises imaging a coherent speckle pattern propagating from an object, using an imaging system being focused on a plane displaced from the object.

U.S. Pat. No. 9,636,041 presents a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

General Description

There is a need in the art for a non-invasive technique for accurately measuring and monitoring characteristics of a region of interest of an individual. The present technique utilizes optical monitoring of a sample for determining biomechanical features such as pressure and elasticity of tissue. The technique is based on monitoring response of the inspected tissue to external stimulation of a selected profile, and utilizes determining parameters associated with damping factor of the tissue with respect to the stimulation. Such characteristics may be associated with one or more conditions that may indicate illness such as variation in intraocular pressure and variation in tissue characteristics, which may be indicative of the existence of lumps within the tissue, e.g. lumps associated with breast cancer conditions.

In this connection the present technique utilizes monitoring a region of interest and determining of one or more damping parameters of the region of interest. The one or more damping parameters are determined by monitoring response of the region of interest to an external stimulation of a selected profile and relaxation of the response over time after stimulation ends.

To this end, the present technique generally utilizes speckle-based monitoring of the region of interest. More specifically, the present technique utilizes illumination of at least a portion of the region of interest with coherent illumination and collecting light components reflected from the illuminated region for collection of at least one sequence of speckle patterns. Generally correlations between the collected speckle patterns provide data indicative of vibrations/movements in the region of interest. Accordingly, speckle-based monitoring is associated with collection of a sequence of image data pieces indicative of secondary speckle patterns formed by self-interference of coherent light reflected/scattered from the region of interest. In some configurations, the reflected light is collected using out-of-focus imaging system to thereby optimize collection of the speckle patterns in the reflected light.

An aspect of some embodiments of the present invention relates to a technique for measuring a characteristic of a region of interest. In the technique, the region of interest is illuminated with a coherent light source, and light returning/scattering from the region is collected for generating a sequence of images (or image data pieces) associated with secondary speckle patterns generated by self-interference of the reflected light. The region of interest is further excited by an external stimulation, such as a sound wave pulse or ultrasound pulse of selected duration. At the end of the pulse, the area of interest's motion keeps vibration, is free damped oscillations until relaxation. The motion of the speckle pattern is measured, for collecting data on vibration of the area of interest for determining one or more damping parameters of the region of interest. Using the determined one or more damping parameters the technique enables determining one or more characteristic of the region of interest, typically using calibration data or pre-provided database.

In some embodiments of the present technique, the region of interest is a subject's eye. The eye is stimulated with a temporally encoded external signal, and, after terminating the stimulation, the eye's free damped oscillation is observed. In other embodiments of the present technique, the region of interest may generally be any region of the subject's body, where the technique is used for detection of under-the-skin impurities by analyzing free damped oscillation of the skin surface. For example, the present technique may be used for detecting breast cancer lumps.

Therefore, an aspect of some embodiments of the present technique relates to a method for determining one or more characteristics of a region of interest. The method includes: providing stimulation for exciting the region of interest for a first selected time period; monitoring mechanical response of the region of interest for at least a second time period after said first time period; processing data indicative of said mechanical response, and determining data on one or more measures of motion of said region of interest; utilizing said data on one or more measures of motion for yielding at least one damping parameter indicative of damping of the mechanical response of the region of interest, and determining at least one characteristic of the region of interest in accordance with said at least one damping parameter.

The monitoring may comprise directing coherent illumination onto at least a portion of said region of interest, collecting light returning from the region of interest using at least one imaging unit defocused with respect to said region of interest and generating a sequence of image data pieces associated with a sequence of secondary speckle patterns formed by self-interference of light components reflected from said region of interest; said processing the data indicative of said mechanical response comprises processing said sequence of image data pieces and determining one or more correlation functions between different image data pieces.

According to some embodiments, processing of said sequence of image data pieces comprises determining at least one time-varying spatial correlation function between speckle patterns in consecutive image data pieces, said at least one time-varying spatial correlation function being indicative of vibrations at said at least a portion of the region of interest.

The determining of a measure of motion may comprise determining variation of said at least one time-varying spatial correlation function between speckle patterns in image data piece collected within said second time period.

In some embodiments of the present invention, providing stimulation comprises generating a predetermined stimulation field in the form of one or more acoustic wave pulses aimed at the region of interest.

The Stimulation may be formed by one or more acoustic wave pulses comprising infrasonic acoustic frequencies. Alternatively, or additionally, the one or more acoustic wave pulses may comprise amplitude modulated sinusoidal waves having a temporal pulse length of up to 1 second.

According to some embodiments of the present invention, yielding said at least one damping parameter comprises processing the one or more measures of motion and determining at least one decay factor of said mechanical response at said at least a portion of the region of interest during said second time period, from a response amplitude of excitation in said first time period to response amplitude being at noise level in said second time period.

The decay factor may comprise a Q-factor indicative of an exponential decay factor in the vibration of the region of interest.

In some embodiments of the present invention, the region of interest comprises at least one region associated with subject's eye, wherein the characteristic is intraocular pressure (IOP).

According to some embodiments of the present invention, the region of interest comprises at least one region associated with a human breast, wherein the characteristic is associated with existence and size of micro calcifications located in breast tissue.

According to some embodiments, yielding at least one damping parameter may comprise determining at least one of: duration of said second time period $\tau$ of a free damped oscillation up to the noise level; effective oscillation action S corresponding to an action of the vibrations of the region of interest; useable oscillation energy fraction G associated with a relation between actual and potential linear decay of oscillation given by: $G=2S/(A_m \tau)$, where $A_m$ is an amplitude of a maximum overshoot in the free damped oscillation.

Another aspect of some embodiments of the present invention relates to a system for use in determining one or more characteristics of a region of interest. The system includes: a stimulation unit configured for providing selected external stimulation at a vicinity of the region of interest, for at least a first time period; a monitoring unit configured for collecting data indicative of mechanical response of at least a portion of said region of interest and generating corresponding mechanical data; a control unit configured for receiving and processing said mechanical data and determining said one or more characteristics of the region of interest, said control unit comprises at least one processing utility configured for receiving said mechanical data and for processing said mechanical data and for determining one or more parameters indicative of damping said mechanical response of said region of interest with respect to external stimulation during a second period following the first period to thereby determine data indicative of said one or more characteristics of the region of interest.

In some embodiments of the present invention, the stimulation unit comprises an acoustic wave generator (speaker unit or transducer unit) configured for providing the selected external stimulation by emitting one or more pulses of acoustic waves aimed at the vicinity of the region of interest.

The acoustic wave generator may be configured for emitting infra or ultra-sonic pulses.

The acoustic wave generator may be configured for emitting amplitude modulated sinusoidal waves having a temporal pulse length of selected duration.

According to some embodiments of the present invention, said monitoring unit is configured as an optical monitoring unit and comprises at least one collection unit, said collection unit comprising an optical imaging arrangement and a detector array and is configured for collecting light returning from the region of interest in response to coherent illumination thereof and forming at least one sequence of defocused images on said detector array for generating at least one sequence of image data pieces associated with secondary speckle patterns formed by self-interference of light components returning from said selected body region in response to said coherent illumination; said mechanical data comprises a plurality of image data pieces indicative of said speckle patterns.

The monitoring unit may further comprise at least one illumination unit configured for providing said coherent illumination of said region of interest.

According to some embodiments, the at least one processing utility may comprise a correlation module configured for receiving said mechanical data in the form of a plurality of image data pieces and for processing said mechanical data for determining at least one time varying spatial correlation function between speckle patterns in consecutive image data pieces, said at least one time varying spatial correlation function being indicative of vibrations at said at least a portion of the region of interest.

According to some embodiments of the present invention, the at least one processing utility comprises a damping module configured for receiving and processing data on the mechanical response of the at least a portion of said region of interest within a second time period, for determining at least one parameter indicative of damping of said mechanical response of said region of interest.

The damping module may be configured for determining said at least one parameter indicative of damping of said mechanical response of said region of interest by determining at least one decay factor of said mechanical response at said at least a portion of the region of interest, said at least one parameter being associated with said at least one decay factor.

The damping module may be configured for determining a Q-factor indicative of an exponential decay factor in the mechanical response of the region of interest.

According to some embodiments of the present invention, the region of interest comprises at least a region of a subject's eye, wherein the one or more characteristics comprise intraocular pressure (IOP).

In some embodiments of the present invention, the region of interest comprises at least a region of a human breast, wherein the one or more characteristics comprises existence and size of micro calcifications located in breast tissue.

In some embodiments, said one or more parameters indicative of damping response comprise at least one of: duration of said second time period $\tau$ of a free damped oscillation up to the noise level; effective oscillation action S corresponding to an action of the vibrations of the region of interest; and useable oscillation energy fraction G associated with a relation between actual and potential linear decay of oscillation given by: $G=2S/(A_m \tau)$, where $A_m$ is an amplitude of a maximum overshoot in the free damped oscillation.

According to some embodiments of the present invention, said control unit further comprises a storage utility comprising pre-stored data indicative of a relation between said one or more parameters indicative of a damping response and at least one medical condition associated with said characteristics of a region of interest; said one or more processing utilities being configured and operable for extracting said pre-stored data in accordance with the determined one or more parameters indicative of the damping response for generating corresponding output data.

BRIEF DESCRIPTION OF THE DRAWINGS

In order to better understand the subject matter that is disclosed herein and to exemplify how it may be carried out in practice, embodiments are now described, by way of non-limiting example only, with reference to the accompanying drawings, in which.

DETAILED DESCRIPTION OF EMBODIMENTS

Figure 1A:
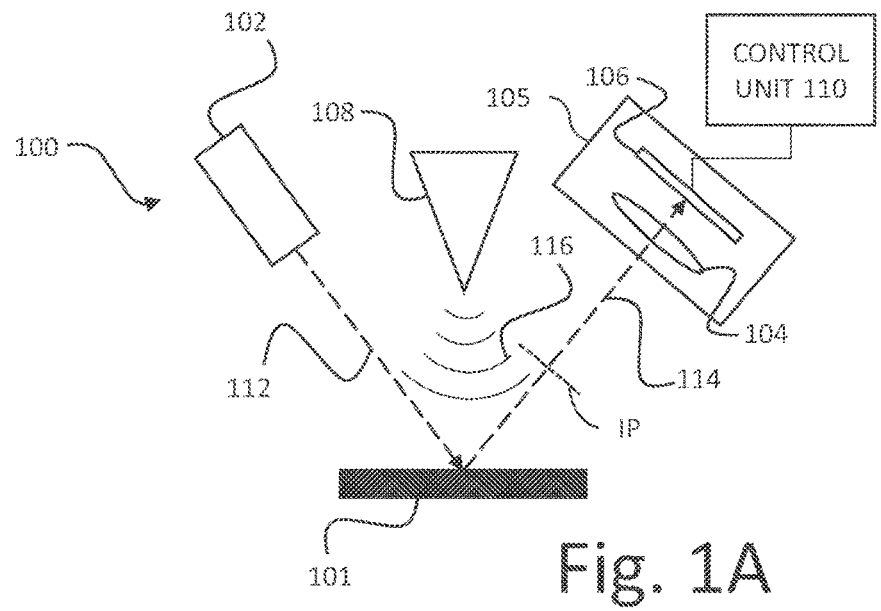
FIGS. 1A and 1B are schematic illustrations of imaging system 100 for detecting motion characteristics of a region of interest (FIG. 1A) and control unit 110 for determining one or more parameters of the region of interest (FIG. 1B) according to some embodiments of the present invention.

Referring now to the drawings, FIG. 1A is a schematic drawing illustrating an imaging system 100 for measuring characteristics of a region of interest 101 of an object.

The system 100 includes an illumination unit 102, a collection unit 105 including an optical imaging arrangement 104 and a detector array 106, a stimulation unit 108 and a control unit 110.

The illumination unit 102 is configured for illuminating the region of interest 101 with a coherent light beam 112. The light reflected/refracted 114 from the region of interest 101 is collected by the optical imaging arrangement 104 and directed onto the detector array 106. The optical imaging arrangement 104 may include a single lens, a plurality of lenses, or any number of optical units configured for receiving the reflected/refracted light 114 and creating a defocused image of the region of interest 101 onto the detector array 106. More specifically, the optical arrangement 104 may be located at a selected location with respect to the detector array 106 and the region of interest 101 for forming, on the detector array, an image corresponding to an intermediate plane located away from the region of interest 101. The image(s) created on the detector are generally in the form of secondary speckle patterns generated by self-interference of light components returning from said selected region of interest 101 (e.g. body region of a subject). Generally the region of interest may be located at a dedicated sample position using a sample holder or sample indication mark, e.g. head-rest or patient seat for easily identifying location of the region of interest.

It should be noted that the collection unit 105 is configured for focusing on a plane which is displaced from a plane of a region of interest 101 to be monitored, i.e. the collection unit 105 is defocused with respect to the region of interest 101. In other words, an object plane IP being imaged onto the detector array 106 by the optical imaging arrangement 104 is displaced from the plane of the region of interest 101, thus producing a defocused image of the region of interest 101 on the detector array 106.

The stimulation unit 108 is configured to controllably provide a stimulation field 116 onto the region of interest 101 that causes a mechanical response (vibrations) in the region of interest. These vibrations cause variations in the speckle patterns collected by the collection unit 105. Generally, according to the present technique, the stimulation unit 108 is configured for providing relatively short (shockwave) stimulation pulses as described further below. The stimulation pulse duration is referred to herein as a first time period. In some embodiments of the present invention, the duration of the pulse is less than 1 second, for example, less than 0.5 seconds, or less than 0.2 seconds. In some embodiments of the present invention, the duration of the pulse is equal to or less than 0.1 seconds.

Generally, changes in position or orientation of the image of the region of interest 101 on the detector array 106 is indicative of the motion (generally tilt or curvature variation) of the region of interest. The control unit 110 receives image data from the collection unit 105, or from the detector array 106 thereof, and determines the motion of the secondary speckle pattern on the detector array 106, as is explained in further detail below.

The stimulation unit 108 may be, for example, an acoustic waves generator (e.g., a speaker), that emits an acoustic wave aimed at the region of interest. The acoustic wave may be infrasonic, sonic or ultrasonic pulse. The stimulation pulse may be amplitude modulated sinusoidal wave with a short temporal duration. After the end of the first period, the stimulation unit 108 does not generate an additional stimulation field and the region of interest is left to vibrate freely for a second period. Generally, with body regions, the free vibration is a damped motion (free damped oscillations).

The control unit 110 is configured for receiving input data indicative of at least one sequence of image data pieces from the detector array 106, and for processing the input data for determining one or more parameters indicative of damping of the response of the region of interest 101 to the external stimulation. As is shown below, the inventors of the present invention found a correlation between the damping parameters of the region of interest and one or more medical conditions of a subject. Therefore, determining the corresponding one or more damping parameters may assist in diagnosis of the one or more medical conditions of the subject. Generally, the control unit 110 may additionally be configured for operating the stimulation unit 108, as well as the illumination unit 102 and collection unit 105 to thereby manage said first and second time periods and illumination pattern of the region of interest 101.

Figure 1B:
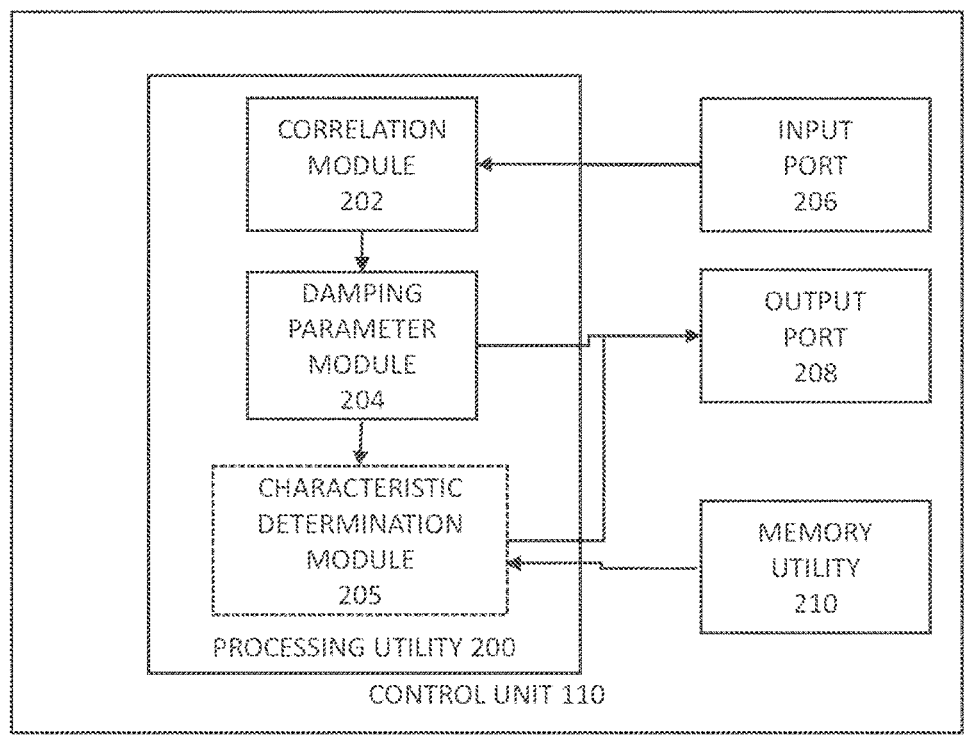

FIG. 1B is a box diagram illustrating a control unit 110 configured for processing image data, according to some embodiments of the present invention.

The control unit 110 includes an input port 206 connected to the detector array 106 and configured for receiving measured data indicative of the detected speckle pattern from the detector array's illuminated pixel(s), a processing utility 200, a memory utility 210, and an output port 208, which may be associated with user interface (data presentation utility), external storage device or any other communication port as the case may be. The processing utility 200 generally includes one or more processors and may further include one or more software/hardware utilities for specific functions including at least a correlation module 202 and damping parameter module 204. In some configurations, the processing utility 200 may also include additional modules such as characteristics determination module 205 (shown in a dashed line as it may be a separate unit used in post processing and may not be part of the system) as well as noise filtering, motions compensation and other modules that are not specifically shown here.

The processing utility 200 is configured for receiving input data indicative of a sequence of image data pieces, determining one or more speckle patterns within the image data pieces, and determining one or more spatial correlation functions between speckle patterns in consecutive image data pieces. Data on the spatial correlation function(s) may be stored in the memory utility 210 or transmitted to a remote storage utility for further processing and later use, and is typically processed by the processing utility in real time, or almost in real time.

The correlation module 202 is configured for processing input image data pieces and determining one or more correlation functions between image data pieces in accordance with a preselected temporal sequence (e.g. consecutive images). The correlation module 202 is further configured for determining a time varying correlation function corresponding to the one or more spatial correlation functions between the different image data pieces. The time varying correlation function is indicative of spatial variations (vibrations, mechanical response to the stimulation) of the region of interest 101. The correlation module 202 may analyze the spatial correlation function for extracting one or more features associated with vibrations (mechanical response) of the region of interest 101 in accordance with data on the first and second time periods associated with operation of the stimulation unit 108 for processing of the damping response of the region of interest.

The damping parameter module 204 is configured and operable for receiving data on the time varying correlation function from the correlation module 202 (or from a local or remote storage unit) and analyzing the correlation function in the second time period for determining one or more parameters of the region of interest indicative of damping of the free oscillations thereof. For example, the damping parameter module 204 may be configured for selectively determining one or more of Q-factor damping parameters, periods of free oscillation up to noise level, effective oscillation action and usable oscillation energy fraction. Generally, the damping parameter module may be selectively operated in one or more selected models in accordance with specific use and operation instructions given via an input user interface and/or stored in the memory utility 210, for selecting the relevant damping parameters. To this end, the damping parameter module 204 is configured for analyzing features of the time-varying correlation module that are indicative of reduction in oscillation/vibrations amplitude of the region of interest in the second time period, and extracting therefrom the one or more parameters of the damping.

It should be noted that the Q-factor is a dimensionless parameter that describes how underdamped an oscillator or resonator is, and characterizes a resonator's bandwidth relative to its center frequency. A higher Q-factor indicates a lower rate of energy loss relative to the stored energy of the resonator; the oscillations die out more slowly.

The characteristics determination module 205 is configured for receiving data on the one or more damping parameters from the damping parameter module 204 (or from a corresponding local or remote memory unit) and processing the damping parameters in accordance with one or more selected models indicative of the condition of the subject to be determined, to determine one or more properties of a the region of interest, e.g. of the body part of the subject. Generally the characteristics determination module 205 may utilize one or more corresponding functions or look-up tables that may be pre-stored in the memory utility 210.

Thus, the processing utility 200 analyzes the spatial correlation function and identifies therein the values of one or more of the parameters. Once the parameters are extracted from temporal variations in the spatial correlation function, the processing utility 200 operates for determining one or more conditions of the region of interest, according to the selected model. Typically, the processing utility 200 may provide an output signal to an operator indicative of the one or more conditions, and/or transmit the determined data (and intermediate data as the case may be) for further processing and storage.

As described more specifically further below, the one or more parameters relating to the temporal change in the spatial correlation function may include a Q-factor, which is indicative of an exponential decay factor in the vibration of the region of interest; a time period $\tau$ of a free damped oscillation up to the noise level; an effective oscillation action S corresponding to action of the vibration of the region of interest; useable energy fraction G associated with a relation between actual and potential linear decay of oscillation given by: $G=2S/(A_m \tau)$, where $A_m$ is an amplitude of a maximum overshoot in the free damped oscillation.

The output port 208 is configured for transmitting output data from the control unit to one or more output devices (e.g. display, printer, speaker), or to the monitor of the control unit, in order to present data to a user. The output data may include a graph of the temporal changes in the spatial correlation function and/or values of one or more of the extracted parameters, and/or values indicative of the condition of the region of interest. The output port may also be associated with the communication port for transmitting data via one or more communication networks, and/or connection to a remote memory utility.

Figure 2:
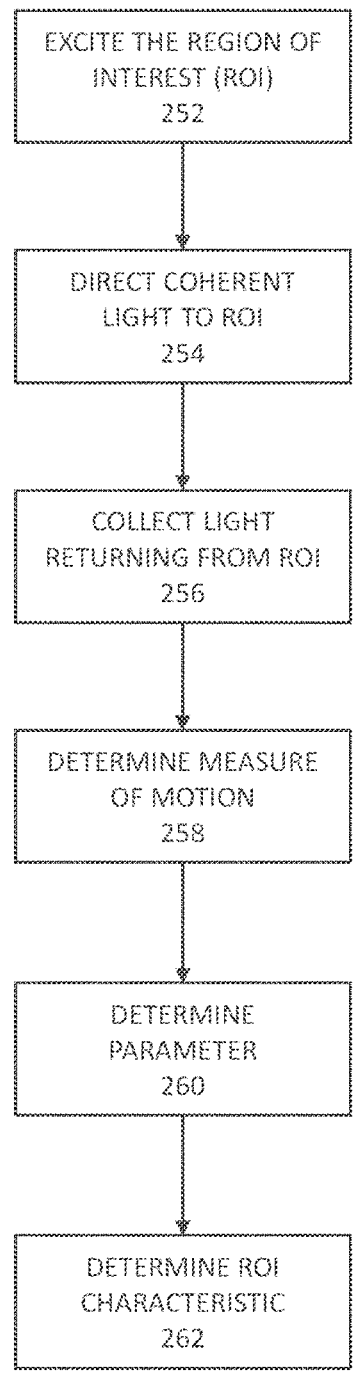
FIG. 2 is a box diagram illustrating certain aspects of a technique for determining characteristic of tissue according to some embodiments of the present invention.

FIG. 2 is a flowchart 250 illustrating certain aspects of a technique for determining characteristics of tissue as described herein. As shown, the technique includes providing excitation onto the region of interest (252) for a selected first time period. At the same time, and especially during a second time period after excitation has stopped, the technique includes monitoring of one or more vibration parameters of the regions of interest (254), such monitoring possibly utilizing speckle-based monitoring (256), or any other suitable monitoring technique. The monitored data is collected and the technique utilizes processing of the collected data for determining one or more measures of motion (258) of the region of interest within the second time period after excitation has ended. Using the motion data, typically until vibrations of the region of interest have diminished and effectively stopped, the technique utilizes determining one or more damping parameters (260), and, based on the damping parameter(s), determining one or more desired properties/characteristics of the region of interest (262).

At 252, a predetermined stimulation is generated for exciting the region of interest during a first selected time period. A second time period begins when the stimulation (and therefore the first time period) ends. As mentioned above, the stimulation may include an acoustic wave pulse, alternating magnetic or electric fields, or any other stimulation type. When acoustic waves are used, the waves may be in the form of one or more pulses, and may be infrasonic, sonic or ultrasonic waves. In some configurations, the stimulation field may be a sinusoidal wave being amplitude modulated with a short temporal pulse (e.g. a pulse duration of one or more seconds).

At 254, the technique utilizes monitoring of a vibration response of the region of interest. The technique may utilize various monitoring methods, which provide high resolution data on the vibration response of the region. Typically, the monitoring may be operated within the first time period, and proceed for at least a second time period after end of the excitation field and until the vibration response is reduced to noise level. As indicated above, the technique may utilize speckle based monitoring (256) using directing coherent light to the region of interest and collecting a plurality of image data pieces associated with secondary speckle patterns returning from the illuminated region.

At 258, the technique utilizes processing of the collected data for determining one or more measures of motion of the region of interest for the second time period after the end of excitation. In the speckle-based monitoring example, one or more sequences of image data pieces are processed to determine corresponding measures of motion of the region of interest, e.g. using one or more correlation functions between consecutive speckle patterns. In some configurations, determining the one or more measures of motion may include determining at least one time-varying spatial correlation function between speckle patterns within the sequence of monitoring data pieces.

At 260, determining one or more damping parameters is exemplified. Generally, the measure(s) of motion are processed within the second time period for determining at least one parameter indicative of damping of the response of the region of interest. The one or more damping parameters may be associated with at least one decay factor of the vibrations in at least a portion of the region of interest. The parameters are then used for determining a characteristic of the region of interest at 262. The characteristic may be determined by using a predetermined function or a look-up table relating the characteristic to the parameter.

Figure 3:
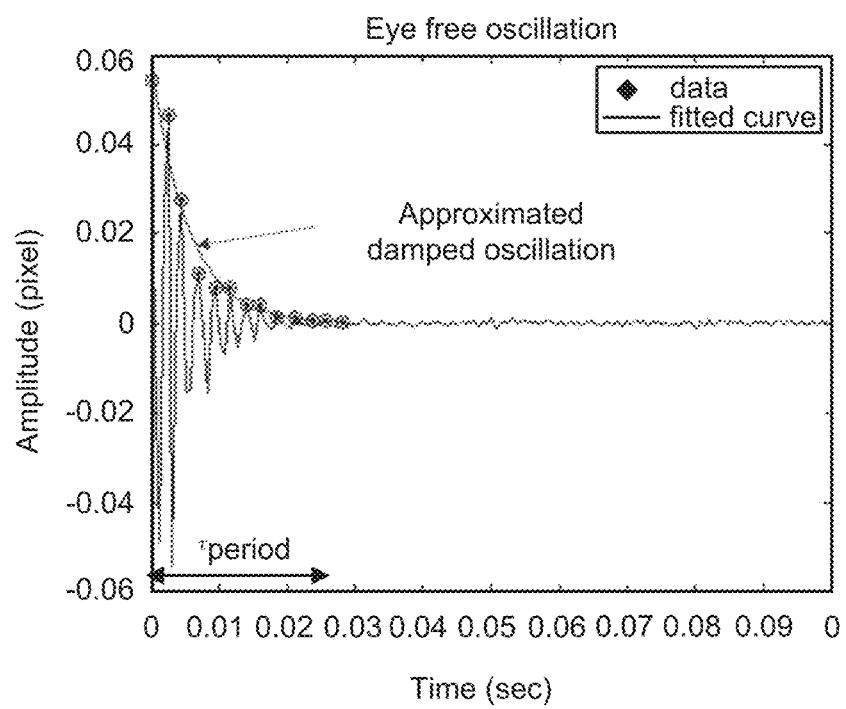
FIGS. 3 and 4 are graphs showing respectively free oscillation of the surface of an artificial eye after the end of a stimulation, and the overshoot seen in the vibration signal of the artificial eye's surface.
Figure 4:
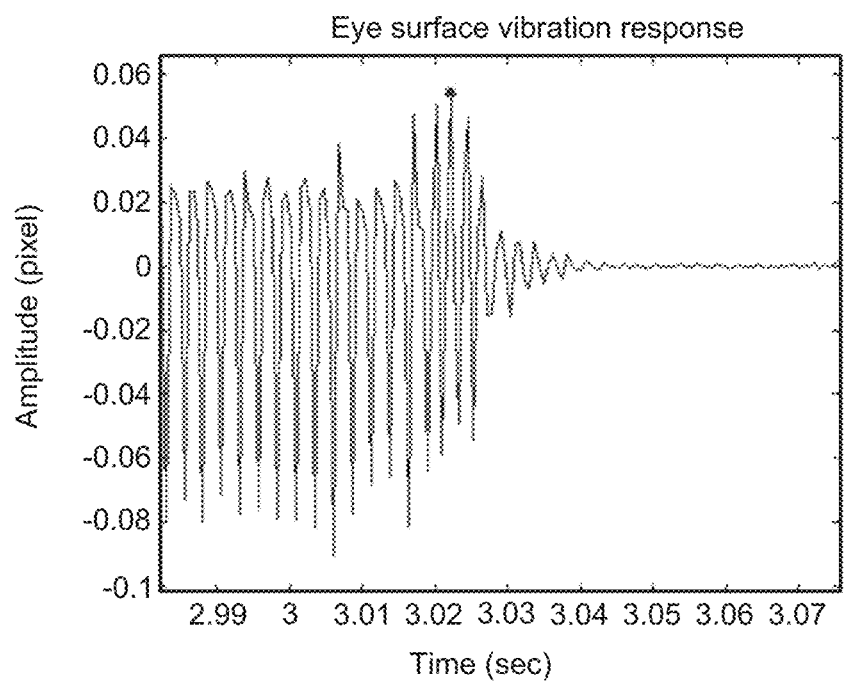

FIGS. 3 and 4 are graphs showing, respectively, free oscillation of the surface of a region of interest, in this non-limiting example an artificial eye, after the end of a stimulation, and the overshoot seen in the vibration signal of the artificial eye's surface.

These graphs are used herein to exemplify how a Q-factor can be measured in an experimental setup.

In reference [1], work in IOP measurements with secondary speckles tracking presents initial steps for an original ability that facilitates noncontact and remote monitoring of IOP using a speaker, a laser and a camera. The defocused camera transforms the tilting movement into the transversal shift of the speckle patterns. The requirement for the focal length f is:

$$f = \frac{K \Delta x Z_3 D}{Z_2 \lambda} \quad \text{(equation 1)}$$

where $\Delta x$ is the size of the pixel in the detector, $Z_3$ is the distance between the secondary speckle and the imaging module, $Z_2$ is the distance between the illuminated surface and the secondary speckle (due to defocusing), $\lambda$ is the laser wavelength, D is the laser spot diameter and it is assumed that every speckle in this plane is seen at least by K pixels. $Z_2$ needs to fulfill the far field approximation:

$$Z_2 > \frac{D^2}{4\lambda} \quad \text{(equation 2)}$$

The Q-factor is a dimensionless parameter that indicates the energy losses within a resonant element during free damped oscillation (see FIG. 3). The Q-factor calculation starts from an overshoot which appears in almost every measurement and can be seen in FIG. 4. Overshoot refers to the transitory values of any parameter that exceeds its steady state. The Q-factor automatic calculation algorithm was developed using known and commercially available mathematical calculation tools (e.g. using Matlab).

The differential equation for the forced harmonic oscillator is $$F(t) = m\frac{d^2x}{dt^2} + \gamma m \frac{dx}{dt} + m\omega_0^2 x \quad \text{(equation 3)}$$

where F(t) is the outside agitation force, m is the object mass, x is the position of the object with respect to the equilibrium position, t is time, $\gamma$ is the damping coefficient and $\omega_0$ the resonant frequency.

A damped transient motion is a solution of the differential equation when there is no force present (the system is driven by a force for a while, and then it is stopped) so F(t)=0. Therefore, if the resonant frequency of $\omega$ is denoted as $\omega_0$, then the measure of the stored energy at any moment gives:

$$E = E_0 e^{-\frac{\omega_0 t}{Q}} = E_0 e^{-\gamma t} \quad \text{(equation 4)}$$

So, the solution for the damped transient motion is an oscillation of frequency close to the resonance frequency $\omega_0$, in which the amplitude of the sine-wave motion diminishes as $$e^{-\frac{\gamma t}{2}}$$

$$x(t) = A_0 e^{\frac{\gamma t}{2}} \cos(\omega_0 t) \quad \text{(equation 5)}$$

In an experiment conducted by the inventors, the damping peaks were evaluated and an exponential fit was matched to the free oscillation damping part. The $\tau_{period}$ (see FIG. 3) was derived from the graph, the $\beta$ (exponential decay constant) was extracted from the fit and eventually the Q-factor was found by Eq. (6).

$$Q_{factor} = \sum_{i=1}^{n} \frac{\pi}{n \beta_i \bar{\tau}_{period}} \quad \text{(equation 6)}$$

where n is the number of repeated tests and $\bar{\tau}_{period_i}$ is the average period per tested eye.

Figure 19:
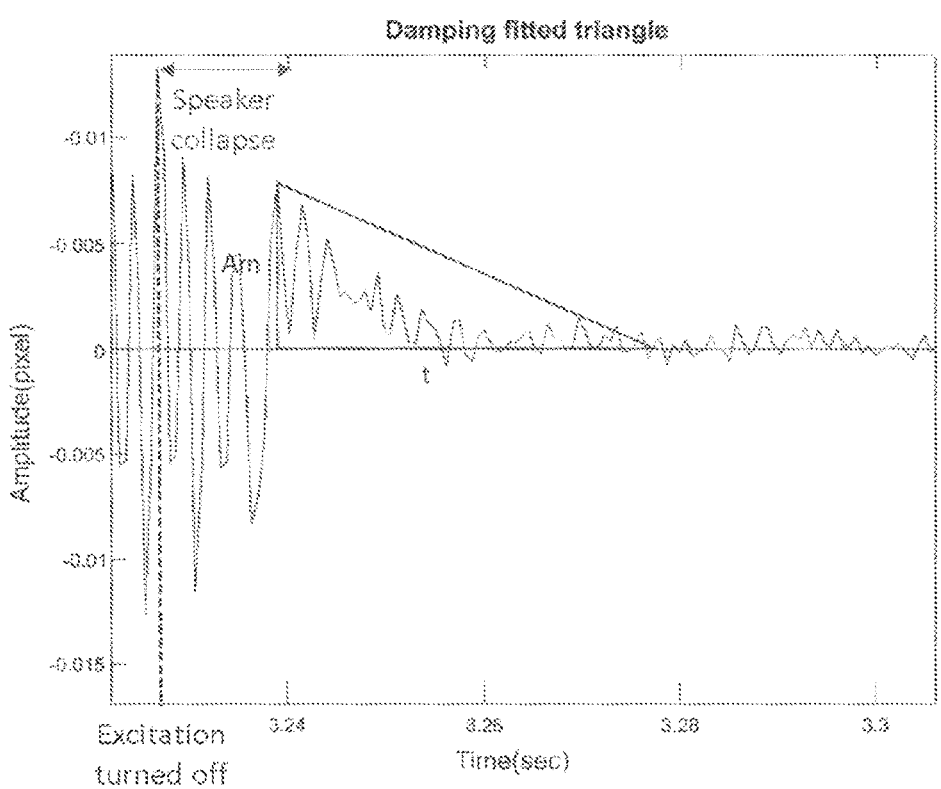
FIG. 19 is a graph illustrating measure free damped oscillation of chicken skin.

FIG. 19 is a graph illustrating a free damped oscillation, in which the region of interest is chicken skin. In FIG. 19, different parameters of the free damped oscillation are extracted from the graph. As shown, such parameters can be related to characteristics of the region of interest. The characteristics of a region of interest can be related to one or more medical conditions of a subject, such as breast cancer under the skin.

The following parameters were defined and determined in order to determine relations between the monitored parameters and elastographic parameters of the inspected sample, which may be indicative of presence and/or size of solid lumps under the sample tissue, in this non-limiting example, diameter and existence of a plastic ball under the layer of chicken skin.

1. Response time, associated with time of the free damped oscillation up to the noise level ($\tau$)
2. The effective oscillation action, defined by the area under the oscillation graph for the same $\tau$ period (S)
3. The useable oscillation energy, as defined by the free damped oscillation area divided by the damping fitted triangle area providing a usable energy fraction parameter (G):

$$G = \frac{2S}{A_m \tau}. \quad \text{(equation 7)}$$

Example 1: Intra Ocular Pressure (IOP)

FIGS. 3-14 relate to the example in which the region of interest in an eye, and the parameters are extracted from the time-varying correlation function which is the Q-factor indicative of an exponential decay factor in the vibration of the eye.

In the present invention, an innovative methodology is presented to evaluate IOP from obtaining a relationship between the Q-factor and the IOP. In order to measure the Q-factor, a sinusoidal sound wave signal agitates the eye surface for a first time period and then is at once turned off. The Q-factor is measured by analyzing data acquired immediately after the signal is turned off and the damped oscillation is observed.

While the Q-factor defined by equation 6 above is extracted via a one-dimensional model, real models of eye surface oscillation may be more complicated, and may contain noise specific to living tissue (e.g. humans) However, the described physical principle can still be applied in this case. The inventors' understanding is based on the idea that there is a strong link between the IOP, the eye surface tension and the damped oscillation reflected by the extracted Q factor.

Except for the Q-factor parameter, the inventors also identified a relation of IOP to a spectrum of variables that are obtained from the measurements. Such variables may include eye vibration frequency, signal amplitude, frequency amplitude and the energy in specific (or selected) frequencies that may be represented by area under the Fourier transform graph, and may also be related to IOP. Additional factors such as corneal thickness, corneal rigidity and elasticity may typically affect accuracy of IOP measurement. In order to take such factors into consideration, the inventors evaluated a correlation between the mentioned parameters, and directly measured IOP (using artificial and animal eye models) and in view of the correlation, the inventors generated a multidimensional linear model of IOP for determining a relation between damping factors and IOP according to the present technique.

Figure 5:
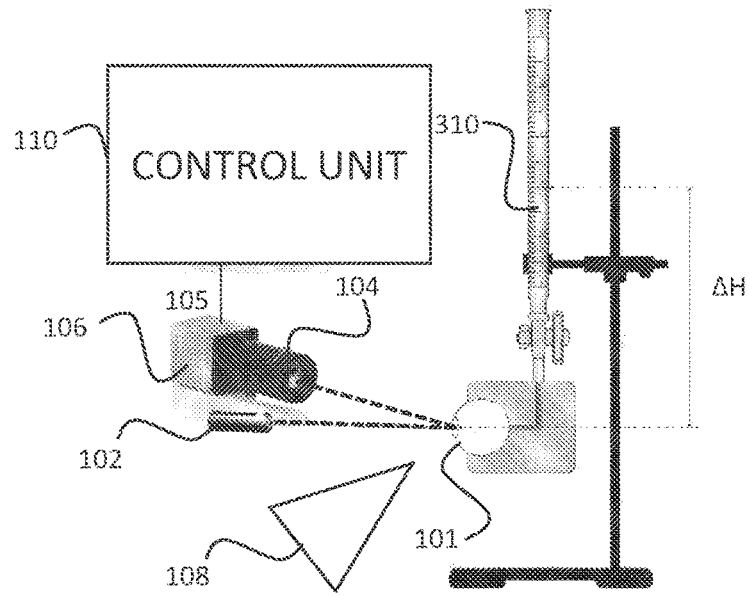
FIG. 5 is a schematic drawing illustrating a system according to some embodiments of the present invention customized for measuring IOP of an artificial eye and of a carp fish eye.
Figure 6:
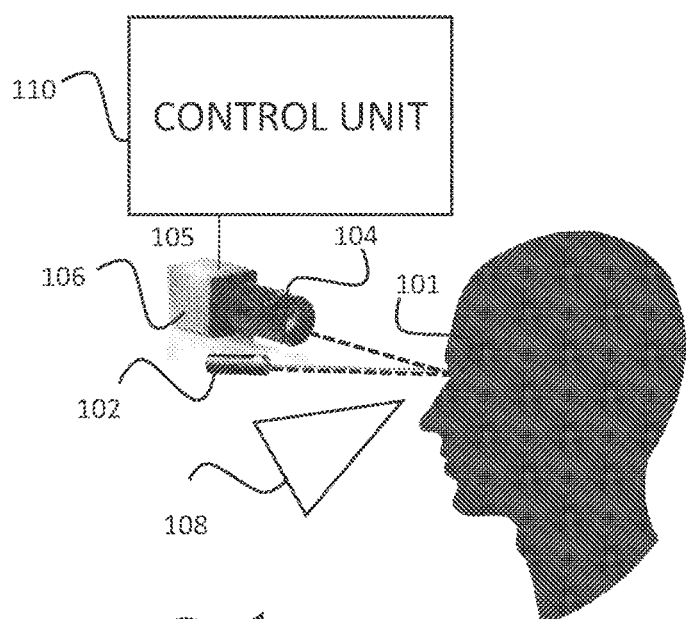
FIG. 6 is a schematic drawing illustrating a system according to some embodiments of the present invention customized for measuring IOP of a human eye on a human subject.

FIG. 5 is a schematic drawing illustrating a system 100 of the present invention customized for measuring IOP of an artificial eye and of a carp (fish) eye, according to some embodiments of the present invention. FIG. 6 is a schematic drawing illustrating the system 100 according to some embodiments of the present invention customized for measuring IOP of a human eye on a human subject.

The system 100 as illustrated in FIGS. 5 and 6 includes all the elements of FIG. 1. FIG. 5 illustrates a system for experimentally measuring IOP from a region of interest 101 being at least a region on the cornea of an artificial eye or a carp eye. The artificial eye and the carp eye are in fluid communication with a calibrated burette 310 that may be filled with water. The IOP of the artificial and carp eyes depends on the height difference $\Delta H$ between the water level and the height of the eye, allowing accurate control of the IOP within the eye 101. In FIG. 6, the region of interest 101 is a region on the cornea or eyelid of a live human eye on a human subject.

In both experimental scenarios performed by the inventors, the collection unit 105 used was a fast camera unit including optical imaging arrangement 104 and detector array 106. The camera unit 105 was positioned at a selected distance (e.g. 35 cm, generally 20 cm up to a few meters) from the sample eye (artificial eye, carp fish eye as illustrated in FIG. 5 or a human eye as illustrated in FIG. 6). The system 100 included an acoustic wave generator 108, e.g. speaker or acoustic transducer, fast camera 105, and a coherent light source 102 (e.g. laser unit) for monitoring of the secondary speckle patterns reflected from the eye and tracking the trajectory of the movement of the inspected surface over time in accordance with the above described technique. The laser unit 102 used in these specific tests was JDS Uniphase CW 1550 nm WDM DFB laser. The reflected light was collected using an "EHD Imaging" InGaAs IK1112 digital camera 105. The camera's focal length was 55 mm with an F-number of 2.8. The illuminating beam was 3 mm in diameter. The camera unit 105 was focused on a focal plane that fulfilled the far field conditions of diffraction applied with respect to the cornea (acting as a back reflecting surface). Specifically, the focusing plane was a few meters away from the cornea. The cornea was stimulated by sound waves with an excitation frequency of 390 Hz, being selected after a sweep on frequencies between 130-1300 Hz, as providing significant response, using an external acoustic wave generator and speaker, which caused the eye surface to vibrate. Each frame of the camera's output showed a secondary speckle pattern. Each frame was correlated to the next frame using dedicated software. The inventors extracted the position of the correlation peak between frames and determined its time varying position where the amplitude denotes the shift in the position of the correlation peak in pixel units of the camera as shown in FIG. 6. The varying time positions in different dimensions/axes are collected for determining a total movement vector. It should be note that diffraction od the speckles and generation of speckle patterns occurs at a wide angle and thus there are generally no constrains on location of the camera unit 104 and 106.

Example 1.1—Artificial Eye

As described above with reference to FIG. 5, the preset technique is testes by evaluating IOP the relation between the Q-factor of free damped oscillation on and artificial eye. For this test, a set of artificial eyes was selected (generally from Kowa LTD). The artificial eyes are made of silicon-based polymer with the following average parameters: Density 1.7 t/m3, Poisson ratio 0.48, Young's modulus 0.025 GPa, Elastic limit 3.4 Mpa. The pressure in the artificial eyes was set by connecting a burette filled with water to the eye. Eye pressure levels ranged between 8-40 mm with 4 mmHg step equivalent to 13.2 cm of water column as illustrated in FIG. 5.

Figure 7:
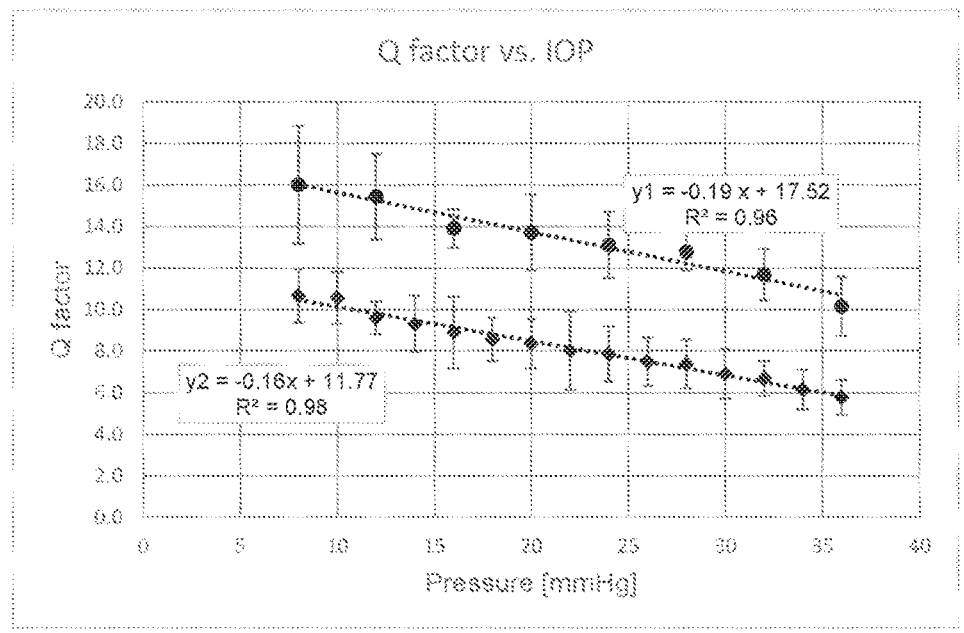
FIG. 7 is a graph illustrating an experimental relation between the Q-factor and IOP in an artificial eye.

The measurement included 10 repeating measurements for each pressure. The tests were performed on two sample eyes having different corneal thicknesses of 0.18 mm (y1) and 0.25 mm (y2). Three results were removed per set of 10 measurements (farthest from average). Before final testing, the variation coefficient was found and the sample size was estimated (see Eq. (8)). For the assessment, the 95% Confidence Interval (CI) with a 10% selected accuracy (margin of error) was used. The detected sample size was 6, so a total of 10 repetitions was sufficient.

$$\text{sample size} = Z^2_{\alpha/2, 95\% CI} * \frac{\sigma^2}{E^2} = 1.96^2 * \frac{\sigma^2}{0.1\mu^2} \quad \text{(equation 8)}$$

where $\mu$ is the mean, $\sigma$ is the standard deviation, $Z\alpha_{/2, 95\% CI}$ is the 95% CI and E is the margin of error. The IOP level vs. the Q-factor results are shown in FIG. 7, showing plot y1 for measurement results on eye with corneal thickness of 0.18 mm and plot y2 for measurement results on eye with corneal thickness of 0.25 mm.

The inventors used the multidimensional model in order to evaluate the IOP from the measured and processed parameters for the eye sample having corneal thickness of 0.25 mm. The relationship between the selected input parameters and IOP was modeled by fitting a linear equation to the collected data. The initial input variables include the following parameters: Q-factor, oscillation frequency (within the damping area), the signal amplitude of the pixel difference graph, amplitude of response at the excitation frequency (390 Hz) as determined by Fourier Transform analysis, which indicates the signal energy at that frequency, and the area under the Fourier transform graph indicating the signal's total energy. The correlation between the damping Q factor and the directly measured IOP were found to have statistically significant linear correlation (r=−0.99, −0.44 respectively).

Figure 8:
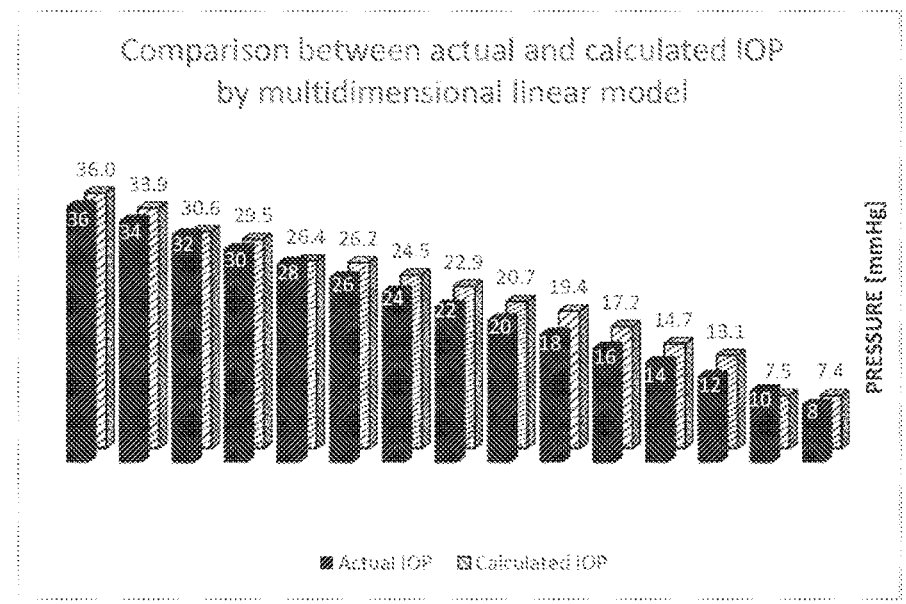
FIG. 8 is a graph illustrating a comparison between IOP of an artificial eye determined experimentally using the technique of the present invention.

When conducting a multidimensional model, a multidimensional correlation coefficient gives the model accuracy. In this case it is $R^2$=0.992, which is close to the one dimensional model result. Thus, it can be concluded that the one-dimensional model is representative enough, and can be used to estimate the IOP. The results of the actual IOP vs. the multiple linear regression results (blue bars) are depicted in FIG. 8 comparing results of IOP measurements using the present technique (calculated IOP) and direct measurement of IOP based on.

Example 1.2—Carp Eye

Figure 9:
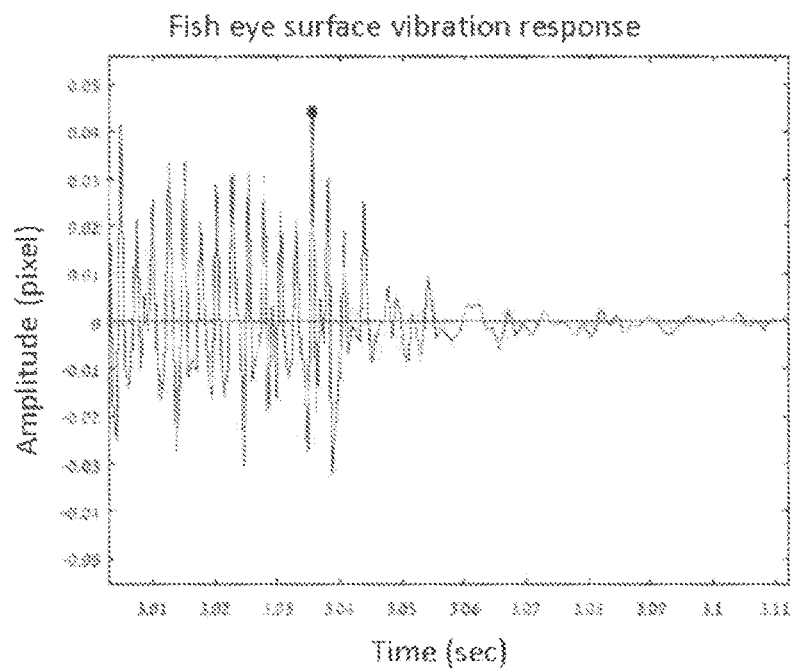
FIGS. 9 and 10 are graphs showing respectively overshoot seen in the vibration signal of the carp fish eye's surface and free oscillation of the surface of a carp fish eye after the end of stimulation.
Figure 10:
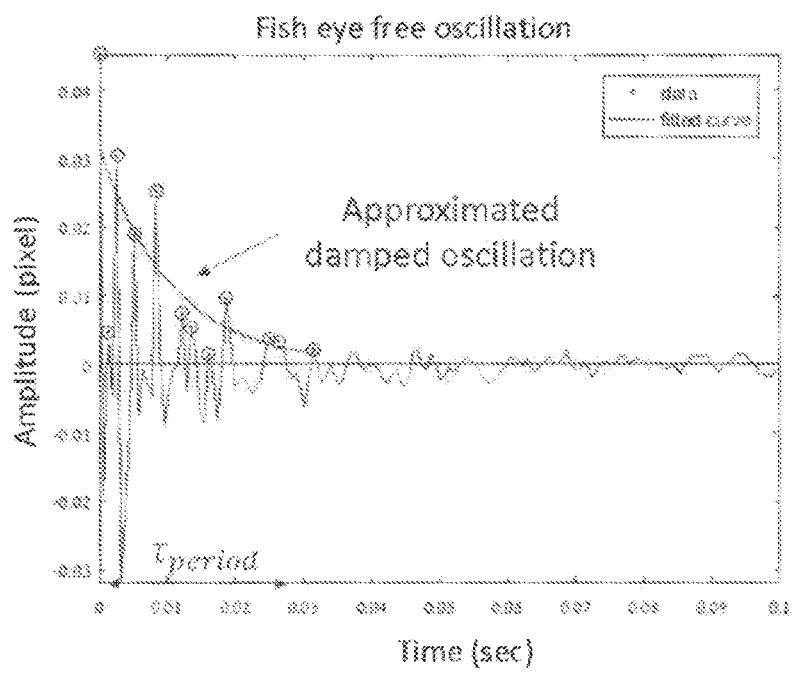
Figure 11:
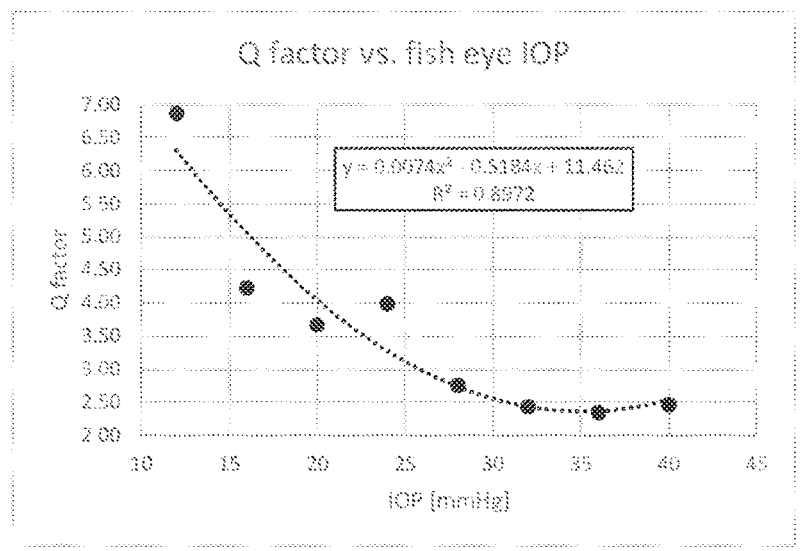
FIG. 11 is a graph illustrating an experimental relation between the Q-factor and measured IOP in a carp fish eye.

The present technique was also tested on a carp fish eye as a first model toward human eye examination. Three carp fish eye globes were acquired from a local distributor within less than 3 hours of postmortem, and experiments were performed within 8 hours of delivery. The experimental setup is the same as described above in FIG. 5 where the artificial eye was replaced by the carp fish eye. The experiment was conducted under the same conditions as the artificial eye test, with eye pressure levels ranging between 12-40 mmHg (with 4 mmHg step). The measurement included 10 repetitions for each pressure as the sample size calculated by Eq. (8) stands at 6. FIGS. 9 to 11 show test results including for vibration amplitudes measured from the fish eye. The overshoot in the fish eye measurement apparent in FIG. 9 and the free oscillation damping area is notable in FIG. 10. The carp fish eye IOP level vs. the Q-factor results are shown in FIG. 11. As shown, the IOP model using fish eye fits to a quadratic model, compared to the artificial eye model that provides linear fit. However, there is a clear decreasing trend allowing high correlation indicated by the $R^2$ value shown in FIG. 11 as being 0.8972, showing a strong correlation between IOP and the Q-factor in the carp fish eye.

Example 1.3—Human Eye

Figure 12:
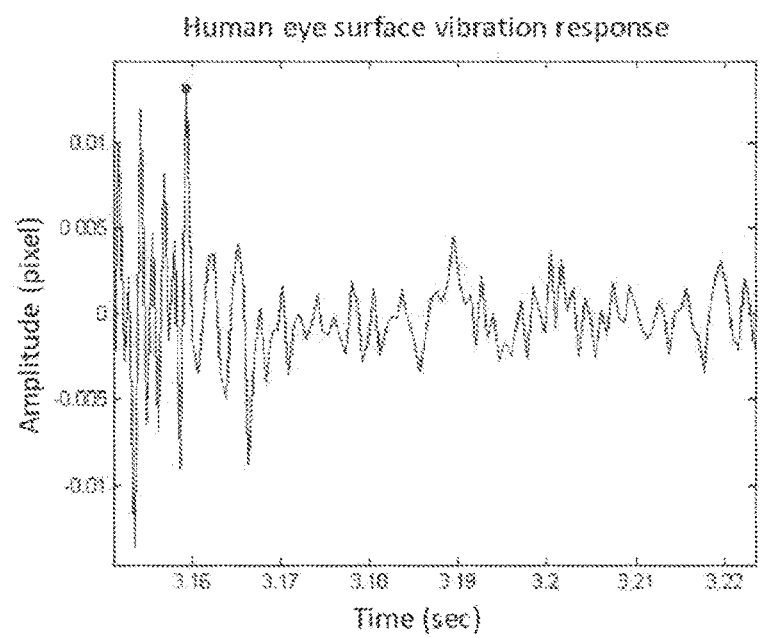
FIGS. 12 and 13 are graphs showing respectively overshoot seen in the vibration signal of the human eye's surface and free oscillation of the surface of a human eye after the end of stimulation.
Figure 13:
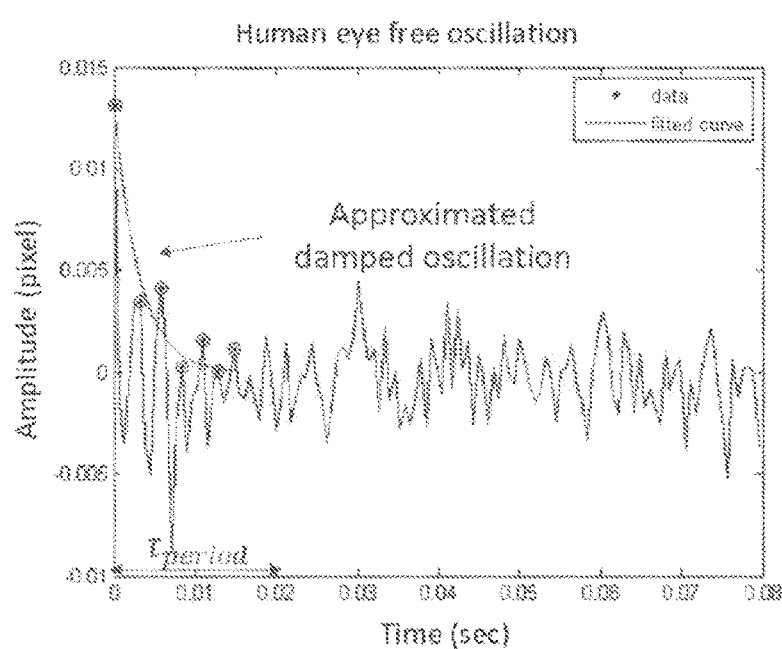
Figure 14:
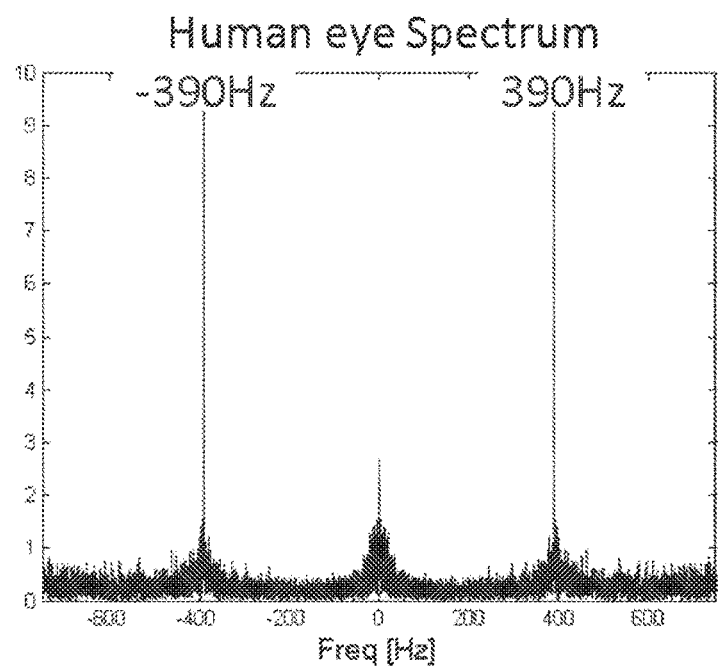
FIG. 14 is a frequency spectrum graph of a human eye stimulated by a sinusoidal ultrasonic wave at a frequency of 390 Hz.
Figure 15:
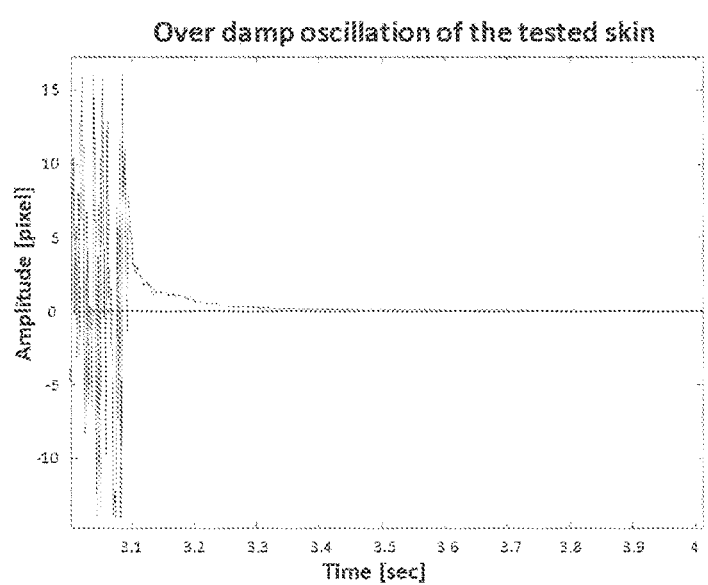
FIG. 15 is a graph illustrating a damped oscillation of chicken breast skin.

The methodology was also applied for IOP measurement on human eyes. To the end the test subjects, including a selected group of individuals between the ages 25-70 years, were instructed to place their face on a head rest including chin and forehead support positioned to provide suitable inspection with respect to the laser light source and camera unit as illustrated in FIG. 6. The subjects' eyes was externally stimulated by sound waves and the response was captured by optically monitoring the cornea. FIGS. 12 and 13 show response of a subject's eye and FIG. 14 shows Fourier components of the measured response. As may be seen from FIG. 12, the overshoot in the human eye measurement is apparent (marked in red) and the free oscillation damping area is notable in FIGS. 12 and 13. The human eye measurements are noisier than the artificial eye ones, which may require certain filtering, longer observation time and/or additional repetitions for averaging to obtain better signal to noise ratio (SNR). FIGS. 12 and 13, show distinct signals with significant SNR collected from human eye. As can be seen in FIG. 14, showing Fourier components of a measurement of a human eye's response to stimulation by a sinusoidal ultrasonic wave at a frequency of 390 Hz, the eye's response is maximal at the excitation frequency, thereby indicating significant detectable signals over the unavoidable white noise.

Example 2—Breast Cancer

Reference is now made to FIGS. 15-22, generally relating to the use of the present technique for determining presence and/or size of a micro calcification in a human breast. In these configurations, the model used is chicken skin having plastic balls beneath the surface of the skin.

Breast tumors associated with micro calcifications are mainly composed of hydroxyapatite, which is a very hard material compared with breast tissue. Therefore, a modality that is sensitive to the elastic properties of tissue would likely be suitable for detection of micro calcifications. This group of imaging techniques is called elasticity imaging. The general approach in elasticity imaging is to measure the response of tissue to an excitation force.

As indicated above, in some embodiments of the present invention, the excitation force is an acoustic pulse of specific frequency. The magnitude of the pressure gradient caused by an acoustic beam travelling through an absorbing medium is proportional to the acoustic intensity in the beam and to the absorption.

During the acoustic wave's propagation in the tissue, the acoustic wave is reflected as a function of the tissue properties and the reflected signal interferes with the agitation signal affecting the surface, resulting in skin oscillation. Once acoustic excitation is stopped, the oscillations reduce in amplitude due to damping. Experiments conducted by the inventors, showed that the presence of cancer tissue, simulated by a plastic ball having different acoustic properties from healthy tissue, affects the damping. The sound wave reflected from the plastic ball increases the oscillation decline and oscillation damps faster. Therefore, the inventors understood that an analysis of the damped oscillations provides prediction on the presence of the plastic ball, or micro calcifications related to breast cancer. The under force damped vibrations of the skin are represented by the free damped oscillator model as known in the art. According to the present technique, the parameters of the tissue (existence and size of lumps) are better determined if the free oscillations are not over damped, as may be observed in experimental results in some frequency ranges, as may be seen for example in FIG. 15.

The general solutions for vibrations x(t) in the free damped oscillator model are described as follows:

$$x(t) = C_1 e^{r_1 t} + C_2 e^{r_2 t} \quad \text{(equation 11)}$$

where $$r_1 = \frac{-b + \sqrt{b^2 - 4k}}{2} \quad \text{(equation 12)}$$

$$r_2 = \frac{-b - \sqrt{b^2 - 4k}}{2}$$

Constants $C_1$ and $C_2$ can be determined from initial condition $x(0) = A_{max}$ (maximum amplitude) and $\dot{x}(0) = 0$, where b is an estimated damping factor and k is the model estimated spring constant and can be determined based on overdamping approximation.

Figure 16:
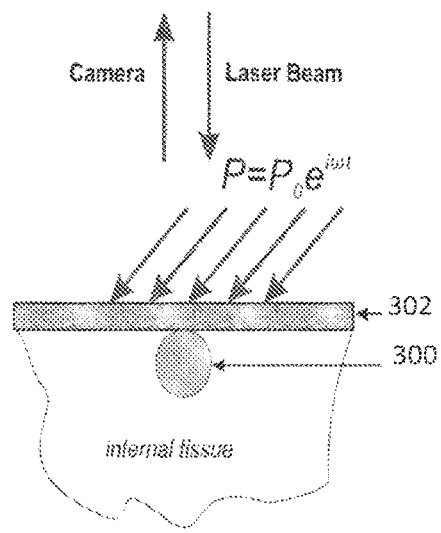
FIG. 16 and is a schematic drawing illustrating a detection technique according to some embodiments of the invention using chicken breast with plasticized balls inserted respectively just under the skin.

The current work is based on the inventors' understanding that micro calcification related to breast tumor can be modeled by means of a plasticized ball inserted in the tissue. This model is illustrated in FIG. 16 showing a plastic ball 300 located under skin tissue 302 and illustrating the stimulation field P and speckle-based monitoring using a camera and a laser beam. Different sizes of plasticized balls 300 were inserted under the chicken breast skin 302 as shown in the figure.

Plastic balls of 2, 4, 6 and 8 mm were prepared for the experiment. As breast simulated tissue, a 2 cm thick chicken breast part covered by skin was used.

At the first stage, the balls were placed directly under the skin inside the tissue so that the top of the balls touched the internal part of the skin as exemplified in FIG. 16. A HJ 532 nm wavelength green laser was used to illuminate the tissue. After acoustic excitation stopped, tissue free oscillation response was evaluated.

Figure 17:
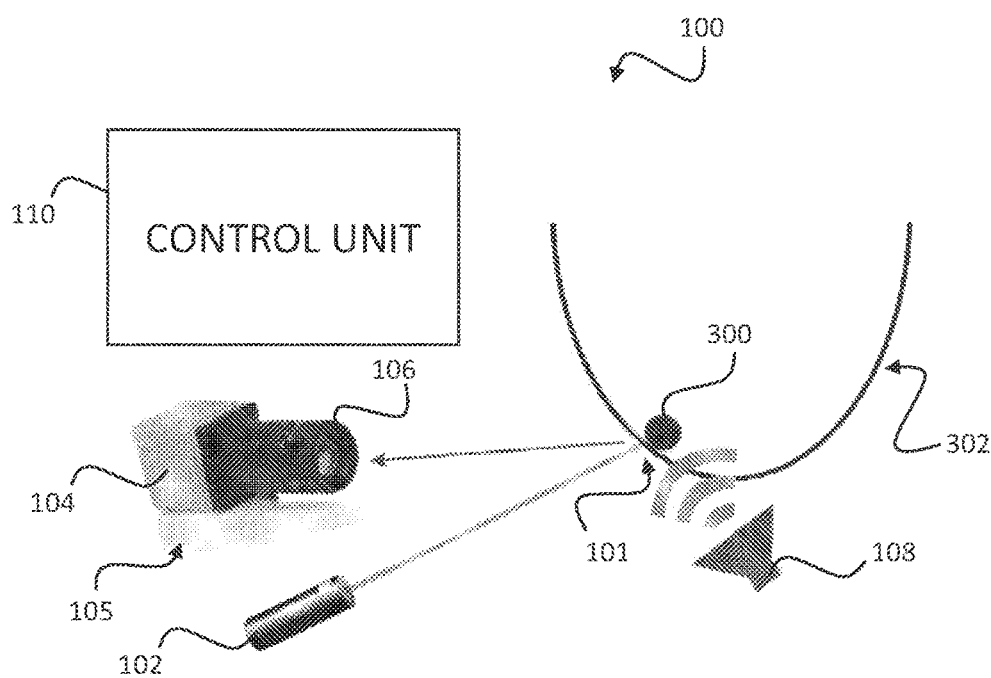
FIG. 17 is a schematic illustration of a system according to some embodiments of the invention for detecting properties of a region of interest of a tissue.

Referring now to FIG. 17, a system 100 for detecting properties of a region of interest of tissue is illustrated, according to some embodiments of the present invention that are generally directed at detecting existence and size of lumps under biological tissue (e.g. cancer lumps such as breast cancer).

The collection unit 105 is optically-based monitoring infrared device/camera including imaging optics 106 and detector array (CCD) 104 positioned at a selected distance from the examined chicken tissue 302. In this specific experimental example, the inspected tissue is chicken breast containing plastic ball 300 located under the skin, and the camera used is a PixeLINK® camera being high sampling rate digital camera, located at a distance of 28.5 cm from the sample surface. Further, the sample is illuminated by illumination unit 102 using a HJ 532 nm green laser. The camera's focal length was 55 mm with an F-number of 2.8. The illuminating beam was 3 mm in diameter. The focusing was performed on a focal plane that fulfills the far field conditions of diffraction applied with respect to the back-reflecting surface, that in this case was the skin. Specifically, the focusing plane was a few meters away from the skin surface. The skin was agitated by sound waves with an excitation frequency of 300 Hz. Each frame presented a secondary speckle pattern being correlated to the next frame. The position of the correlation peak was derived and its time dependent position was plotted using dedicated software. The signal amplitude designates the shift in location of the correlation peak in pixel units of the camera.

Figure 18:
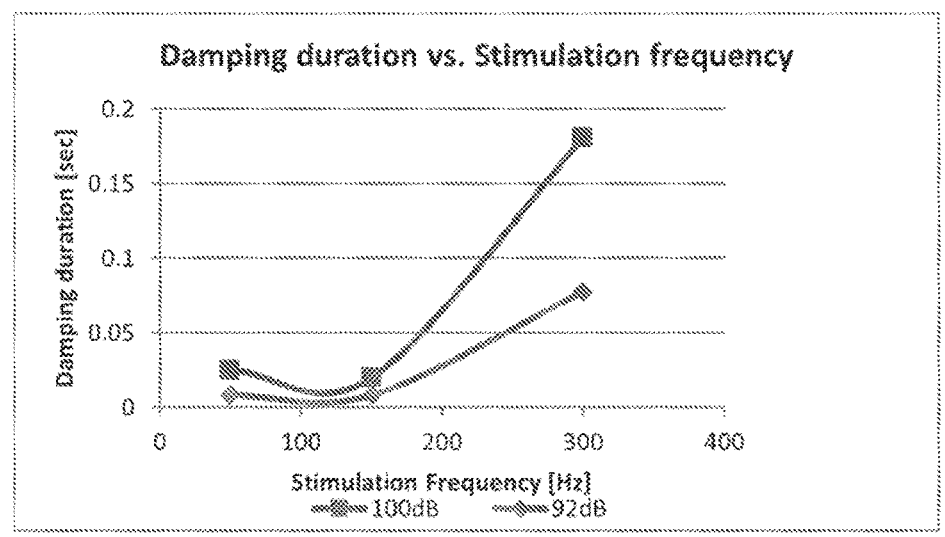
FIG. 18 is a graph illustrating the measured damping duration as a function of stimulation frequency for different sound wave amplitudes.

FIG. 18 is a graph illustrating the measured damping duration as a function of stimulation frequency for different sound wave amplitudes. In order to find preferred/optimal excitation frequency with most significant response, several frequencies within (50-300 Hz) were examined. The frame rate (frames per second—FPS) of the digital camera was three times higher than the frequency measured, in order to fully fulfill the Nyquist ratio requirements. Furthermore, in order to find the most powerful response, the inventors applied the excitation signal under the mentioned frequencies with two different sound wave amplitudes (92 dB and 100 dB). After preliminary tests, based on the damping duration, the agitation frequency of 300 Hz@ 100 dB and camera working at 900 FPS were selected for further experiments in this specific model. This is because the duration of damping from the maximal oscillation amplitude to noise level was higher for a sound frequency of 300 Hz@ 100 dB.

FIG. 19 is a graph illustrating a free damped oscillation of chicken skin, as obtained from the system of FIG. 17, using the above mentioned excitation parameters. In order to detect plastic balls under the skin simulating breast cancer calcification, a chicken breast was used as the examined tissue. Cuts under the skin surface were performed for inserting four balls of different sizes (of 2, 4, 6 and 8 mm in diameter). The top of the balls were positioned directly under the skin surface. As a reference, the tissue was also tested independently without any ball inserted into it. The tissue was excited using sound waves with an acoustic excitation frequency of 300 Hz and an intensity of 100 dB from an external speaker. After agitating the tissue surface for a first time period (for example less than 1 s, less than 0.5 s, or less than 0.1 s), the signal was turned off and the damped free oscillation of the skin was recorded and analyzed for the period when the speaker was turned off until the amplitude of the skin free damped oscillation reached the average noise level.

The following damping parameters were calculated in order to determine the relation of the plastic ball diameter:

1. Time of the free damped oscillation up to the noise level ($\tau$);
2. An effective oscillation action, as determined by the area under the oscillation graph for the same $\tau$ period (S);
3. A usable oscillation energy fraction (G), determined as the effective oscillation action divided by the damping fitted triangle area:

$$G = \frac{2S}{A_m \tau}.$$ (equation 13)

where $\tau$ is the time of the free damped oscillation up to the noise level, S is the area under the oscillation graph for the same $\tau$ period and $A_m$ is the amplitude in maximum overshoot; and 4. Parameters of exponential fit as described above.

Average values, standard deviation and coefficient of variations were calculated for the above-mentioned parameters in order to ensure that the tests, repeated ten times, presented statistically significant results (95% confidence interval with 10% selected margin of error).

Figure 20:
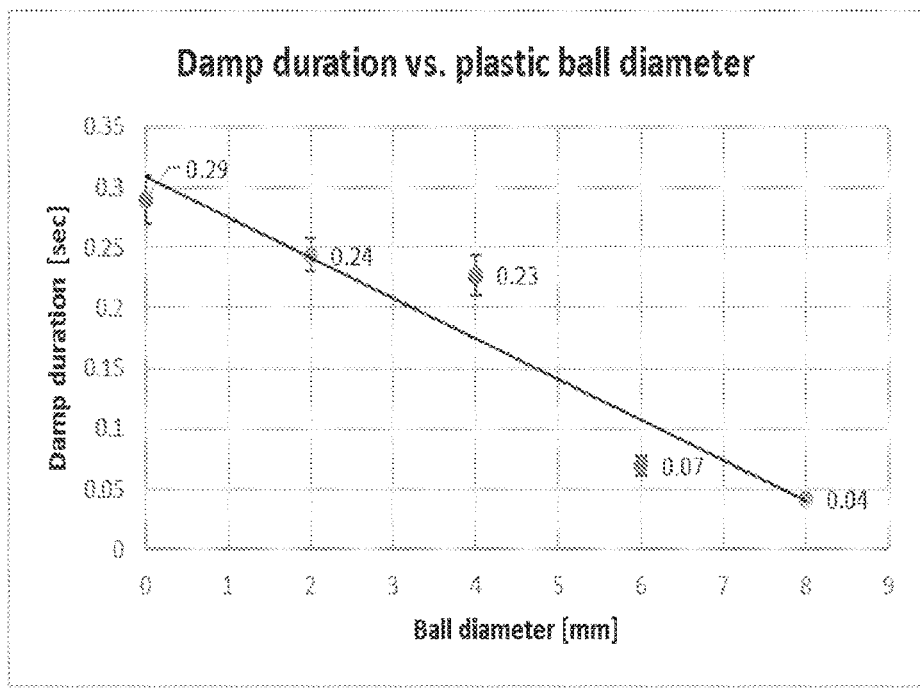
FIG. 20 is a graph showing measured durations of free damped oscillation, up to the noise level, as a function of diameter of the plastic balls located under the region of interest in the skin.
Figure 21:
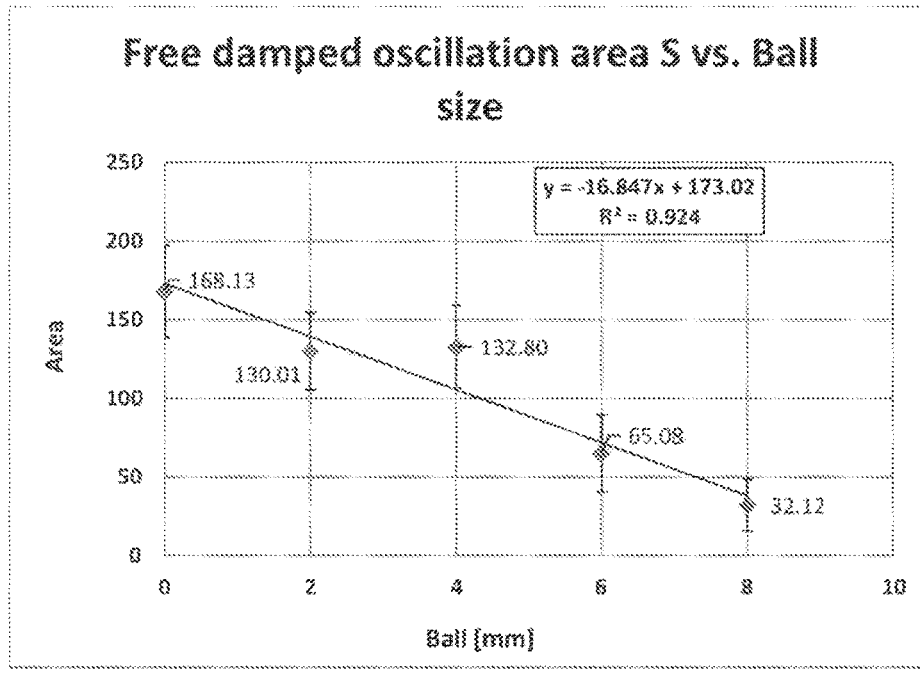
FIG. 21 is a graph showing relation between integrated area under the measured free damped oscillation graph as a function of the diameter of the plastic balls located under the region of interest in the skin.
Figure 22:
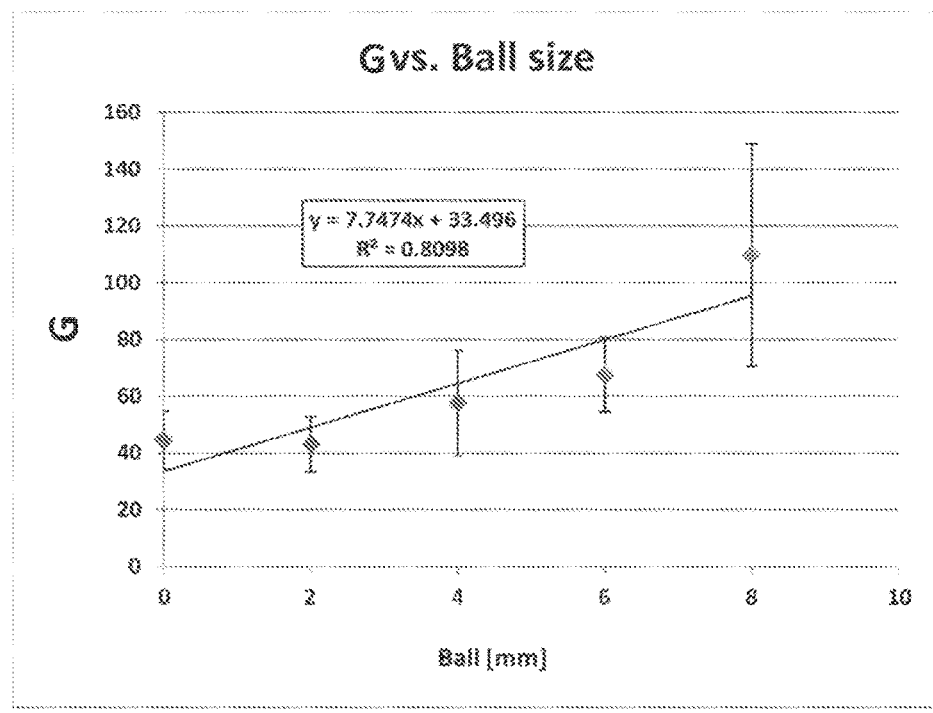
FIG. 22 is a graph showing the usable energy fraction for oscillations as a function of the diameter of the plastic balls located under the region of interest in the skin.

The data obtained from the inventors' experiment shows that parameters 1-3 show strong correlation with the plastic ball size as shown on the FIGS. 20-22, while parameter number 4 above, associated with exponential decay, may provide data indicative of tissue pressure/tension as described above.

FIG. 20 is a graph showing the measured duration of time of the free damped oscillation up to the noise level as a function of the diameter of the plastic balls located under the region of interest in the skin. The $R^2$ value for this graph is above 0.93, which shows high correlation between duration of the time of the free damped oscillation, and the diameter of the plastic balls.

FIG. 21 is a graph showing the oscillation's effective action, as determined in accordance with the area under the measured free damped oscillation, as a function of the diameter of the plastic balls located under the region of interest in the skin. The $R^2$ value for this graph is 0.924, which shows high correlation between the area under the measured free damped oscillation, and the diameter of the plastic balls.

FIG. 22 is a graph showing the usable energy fraction (coefficient G) as defined by equation 13 as a function of the diameter of the plastic balls located under the region of interest in the skin. The $R^2$ value for this graph is 0.8098, which shows high correlation between the usable energy fraction and the diameter of the plastic balls.

The obtained results in FIGS. 20-22 show that the technique of the present invention allows detection of bodies located under the skin, as exemplified for bodies of size 2 mm and higher. Generally, tumors of this size are considered to be in the early stages of breast cancer disease and are difficult to detect using conventional techniques.

In conclusion, the present invention relates, in some embodiments thereof, to a technique for determining one or more characteristics of a region of interest. The technique includes: providing stimulation for exciting the region of interest for a first selected time period; monitoring mechanical response of the region of interest for at least a second time period after said first time period; processing data indicative of said mechanical response and determining data on one or more measures of motion of said region of interest; and utilizing said data on one or more measures of motion for yielding at least one damping parameter indicative of damping of the mechanical response of the region of interest, and determining at least one characteristic of the region of interest in accordance with said at least one damping parameter.

Non-limiting examples showed that the technique of the present invention can be used in order to measure IOP and to detect micro-calcifications under breast skin tissue.

The invention claimed is:

1. A method for determining one or more characteristics of a region of interest in a subject's body, comprising:
controllably operating a stimulation unit to generate a stimulation field in the form of at least one pulse for exciting the region of interest by said at least one pulse of the stimulation field for a first selected time period;
monitoring vibration response of the region of interest for at least a second time period after said first time period, said vibration response being induced by the stimulation field applied to the region of interest during the first time period and comprising free damped oscillation of a surface of the region of interest during said second time period after said first time period, said monitoring comprising performing speckle based imaging of at least a portion of the region of interest during said second time period and generating measured data in the form of a sequence of image data pieces indicative of the free damped oscillation of the surface of the region of interest;
processing said measured data indicative of said free damped oscillation of the surface of the region of interest and, as a result of the processing, determining data on one or more measures of motion of said region of interest;
utilizing said data on one or more measures of motion for yielding at least one damping parameter indicative of damping of said free damped oscillation, said at least one damping parameter comprising at least one of the following: decay factor of the free damped oscillation; duration of the second time period $\tau$ of the free damped oscillation up to a noise level; effective oscillation action S corresponding to an action of vibrations of the region of interest; useable oscillation energy fraction G associated with a relation between actual and potential linear decay of the free damped oscillation; and
utilizing said at least one damped parameter for determining at least one characteristic of the region of interest indicative of a predetermined medical condition of the subject.

2. The method of claim 1, wherein said speckle based imaging comprises: directing coherent illumination onto said at least a portion of said region of interest, detecting, by a detector array, a sequence of secondary speckle patterns being formed by self-interference of light components reflected from said region of interest and being collected during said second time period from said at least a portion of the region of interest by an imaging arrangement defocused with respect to said region of interest, and generating said sequence of the image data pieces; said processing of the measured data comprising determining one or more correlation functions between different image data pieces.

3. The method of claim 2, wherein said determining of one or more measures of motion comprises processing of said sequence of the image data pieces to determine at least one time-varying spatial correlation function between the speckle patterns in consecutive image data pieces, said at least one time-varying spatial correlation function being indicative of vibrations at said at least a portion of the region of interest, and determine variation of said at least one time-varying spatial correlation function between the speckle patterns in the image data pieces collected within said second time period.

4. The method of claim 1, wherein said stimulation field is in forms of one or more acoustic wave pulses aimed at the region of interest.

5. The method of claim 4, wherein the one or more acoustic wave pulses comprise an amplitude modulated sinusoidal wave having temporal pulse length of up to 1 second.

6. The method of claim 1, wherein said yielding said at least one damping parameter comprises processing the one or more measures of motion and determining at least one decay factor of said vibration response comprising a Q-factor indicative of an exponential decay factor in the vibration response of the region of interest.

7. The method of claim 1, wherein the region of interest comprises at least one region associated with subject's eye, wherein the at least one characteristic is intraocular pressure (IOP).

8. The method of claim 1, wherein the region of interest comprises at least one region associated with a human breast, wherein the at least one characteristic is associated with existence and size of micro calcifications located in tissue of the breast.

9. The method of claim 8 wherein said yielding at least one damping parameter comprises determining the useable oscillation energy fraction G associated with the relation between actual and potential linear decay of oscillation given by: $G=2S/(A_m \tau)$, where $A_m$ is an amplitude of a maximum overshoot in the free damped oscillation.

10. A system for use in determining one or more characteristics of a region of interest in a subject's body, the system comprising:
a stimulation unit configured to controllably apply an external stimulation field on the region of interest, for at least a first time period;
a monitoring unit configured for monitoring vibration response of at least a portion of said region of interest for at least a second time period after said first time period, the vibration response being induced by the stimulation field applied during the first time period and comprising free damped oscillation of a surface of the region of interest during said second time period after said first time period, and generating measured data indicative of said free damped oscillation, said monitoring unit comprising an imaging arrangement defocused with respect to said region of interest and a detector array, and being operable to detect, by the detector array, a sequence of secondary speckle patterns collected by the imaging arrangement at least during said second time period from said at least a portion of the region of interest being illuminated by coherent illumination, and generate the measured data comprising a corresponding sequence of image data pieces being indicative of the free damped oscillation;
a control unit comprising at least one processing utility configured to receive and process said measured data and determine one or more damping parameters indicative of the free damped oscillation of said region during the second time period, to thereby determine data indicative of said one or more characteristics of the region of interest, said one or more damping parameters comprising at least one of the following: decay factor of the free damped oscillation; duration of the second time period τ of the free damped oscillation up to a noise level; effective oscillation action S corresponding to an action of vibrations of the region of interest; useable oscillation energy fraction G associated with a relation between actual and potential linear decay of the free damped oscillation, said one or more characteristics of the region of interest being indicative of a medical condition of the subject.

11. The system of claim 10, wherein said stimulation unit comprises an acoustic wave generator configured to produce the external stimulation field in the form of one or more pulses of acoustic waves aimed at the region of interest.

12. The system of claim 11, wherein the acoustic wave generator is configured to emit an amplitude modulated sinusoidal acoustic wave having a temporal pulse length of selected duration.

13. The system of claim 10, wherein said monitoring unit further comprises at least one illumination unit configured for providing said coherent illumination of said region of interest.

14. The system of claim 10, wherein the at least one processing utility comprises a correlation module configured to receive and process said sequence of the image data pieces and determine at least one time varying spatial correlation function between the speckle patterns in consecutive image data pieces, said at least one time varying spatial correlation function being indicative of vibrations at said at least a portion of the region of interest.

15. The system of claim 14, wherein the at least one processing utility comprises a damping parameter module configured to receive, from the correlation module, data indicative of the time varying correlation function and process said data and determine said one or more parameters of the region of interest indicative of said free damped oscillation vibration response of said region of interest.

16. The system of claim 15 wherein the damping parameter module is configured to determine said one or more parameters indicative of said free damped oscillation by determining at least one decay factor of said vibration response at said at least a portion of the region of interest comprising a Q-factor indicative of an exponential decay factor in the vibration response of the region of interest.

17. The system of claim 10, wherein the region of interest comprises at least a region of a subject's eye, wherein the one or more characteristics comprise intraocular pressure (IOP).

18. The system of claim 10, wherein the region of interest comprises at least a region of a human breast, wherein the one or more characteristics comprise existence and size of micro calcifications located in breast tissue.

19. The system of claim 10, wherein said control unit further comprises a storage utility comprising pre-stored data indicative of a relation between said one or more parameters indicative of the free damped oscillation and at least one medical condition associated with said one or more characteristics of the region of interest; said one or more processing utilities being configured and operable for extracting said pre-stored data in accordance with the determined one or more parameters indicative of the free damped oscillation and generating corresponding output data.

20. The system of claim 19, wherein the one or more characteristics comprise intraocular pressure (IOP), said pre-stored data being indicative of the relation between an eye surface tension, the free damped oscillation, and the IOP.

21. The system of claim 20, wherein the processing utility is configured and operable to determine the eye surface tension from evaluation of damping peaks and matching an exponential fit to a free oscillation damping part, and is configured to characterize the free damped oscillation by a Q-factor indicative of an exponential decay factor in the vibration response of the region of interest.

\* \* \* \* \*